United States Patent [19]

Hakim et al.

[11] Patent Number: 4,615,691
[45] Date of Patent: Oct. 7, 1986

[54] SURGICALLY-IMPLANTABLE STEPPING MOTOR

[76] Inventors: Carlos A. Hakim, 3400 Galt Ocean Dr., Apt. 1702 South, Fort Lauderdale, Fla. 33308; Salomon Hakim, Carrera 13, N. 48-26, Bogota, Colombia

[21] Appl. No.: 559,865

[22] Filed: Dec. 8, 1983

[51] Int. Cl.[4] .............................................. A61M 5/00
[52] U.S. Cl. ................................. 604/9; 310/40 MM; 310/181
[58] Field of Search ........................ 604/8–10; 128/1.3–1.5, DIG. 25; 3/1.7; 310/103, 104, 181, 40 MM; 335/138, 139, 272, 306; 137/539, 539.5; 261/DIG. 74

[56] References Cited

U.S. PATENT DOCUMENTS

| | | | |
|---|---|---|---|
| 3,304,449 | 2/1967 | Pohlman | 310/103 |
| 3,378,710 | 4/1968 | Martin, Jr. | 310/104 |
| 3,391,289 | 7/1968 | Danilewicz et al. | 310/103 |
| 3,527,220 | 9/1970 | Summers | 128/1.5 |
| 3,886,948 | 6/1975 | Hakim | 604/9 |
| 4,156,422 | 5/1979 | Hildebrandt et al. | 604/9 |
| 4,340,038 | 7/1982 | McKean | 128/1.3 |
| 4,360,007 | 11/1982 | Levy et al. | 128/1 R |
| 4,443,214 | 4/1984 | Marion | 604/9 |
| 4,540,400 | 9/1985 | Hoover | 604/9 |

OTHER PUBLICATIONS

Conrad, Coleman W., "Stepping Motors", *Machine Design*, Apr. 11, 1974, pp. 78–80.

Primary Examiner—C. Fred Rosenbaum
Assistant Examiner—Mario Costantino
Attorney, Agent, or Firm—G. Roger Lee

[57] ABSTRACT

A stepping motor isolated physically from electrical power sources and powered by the influence of a magnetic field applied from outside the apparatus, the stepping motor including a rotor and one or more stator elements, the stator elements being composed of magnetically soft and permeable material shaped and positioned with respect to the rotor so that when magnetized under the influence of the external field the stator elements strengthen and orient the magnetic field in their vicinities so as to cause movement of the rotor.

18 Claims, 17 Drawing Figures

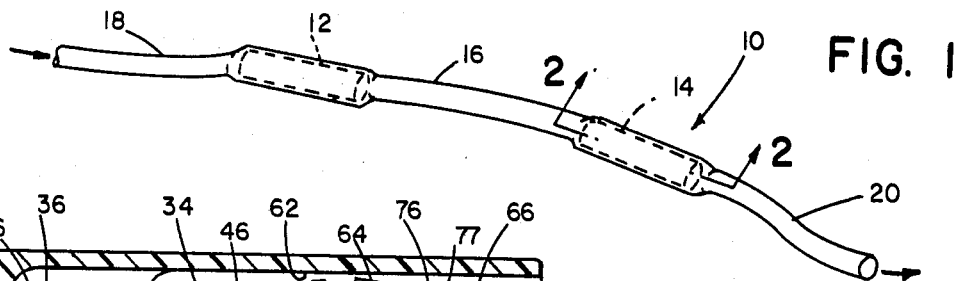
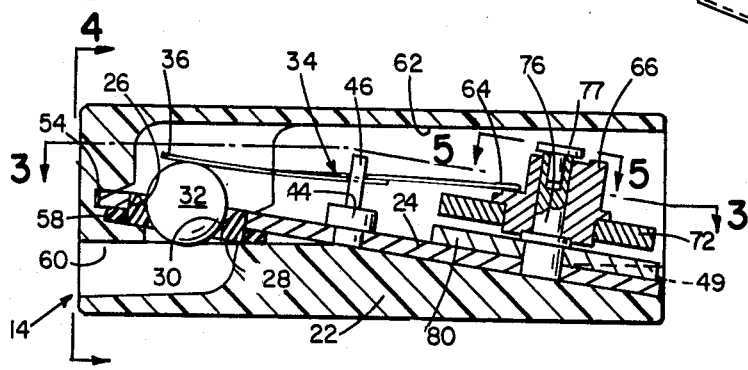
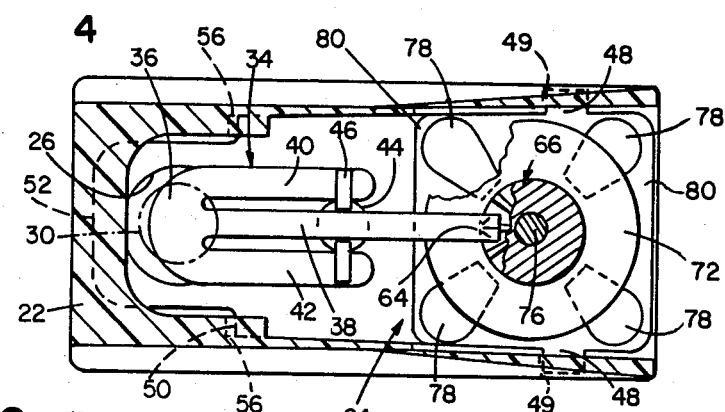
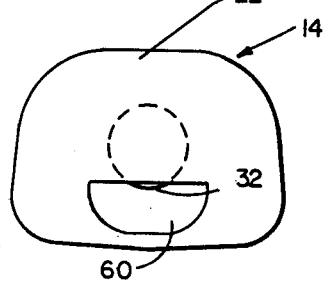
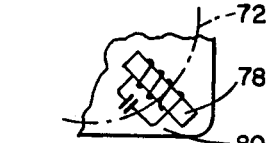
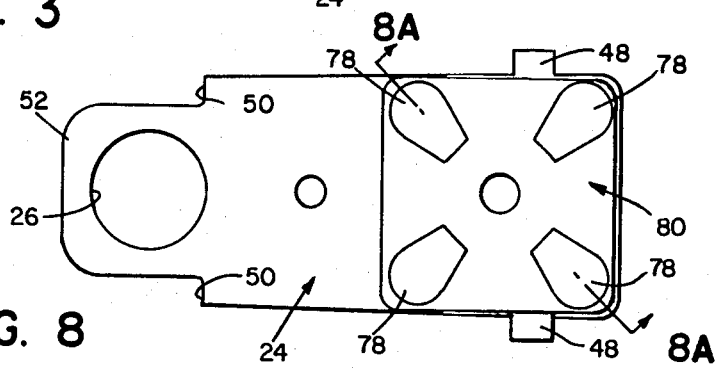
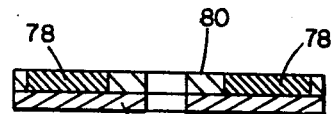
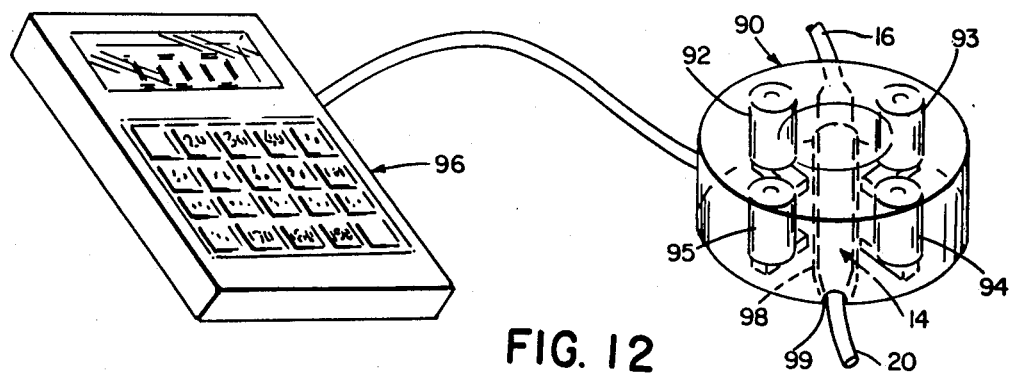

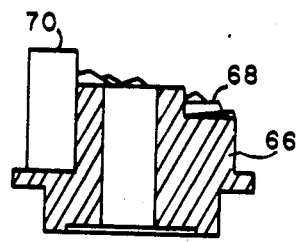
FIG. 6
FIG. 5
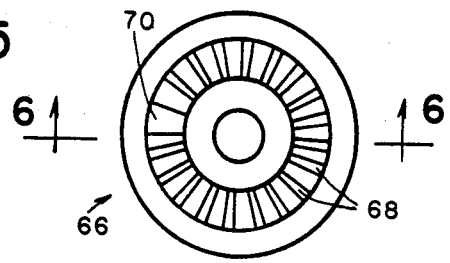
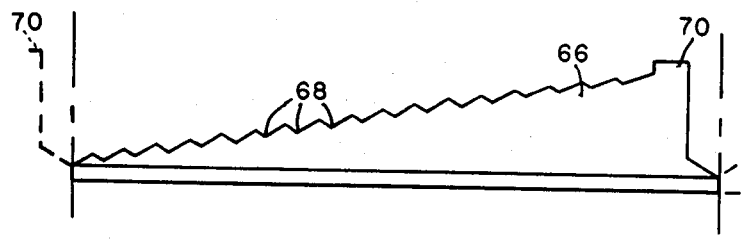
FIG. 7
FIG. 9
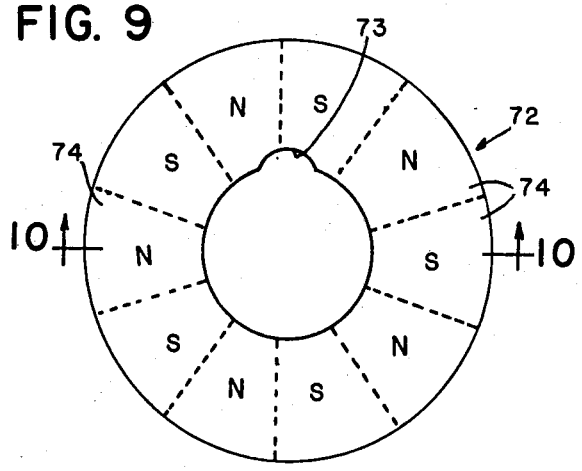
FIG. 10

SURGICALLY-IMPLANTABLE STEPPING MOTOR

BACKGROUND OF THE INVENTION

The invention relates to stepping motors, particularly those for use in surgically-implanted devices.

Stepping motors have been known for many years. The simplest stepping motor consists of a permanent magnet rotor surrounded by a stator made up of four electromagnets. By selectively energizing the electromagnets, it is possible to turn the rotor in angular "steps" of 90°. Often the rotor has a plurality of permanent magnets, so as to reduce the angular step size. Some stepping motors replace the permanent magnets on the rotor with regions of different magnetic reluctance; in these, known as variable reluctance motors, the rotor turns to the position of minimum reluctance. Still others, known as hybrids, combine reluctance differences with permanent magnets.

Stepping motors have been used in some medical applications. For example, they have been used in medical infusion pumps for delivering precise volumetric dosages of drugs at prescribed time intervals. In all these applications the stepping motor was located outside the patient's body, either in a portable device carried by the patient or in a bedside unit.

Other types of medical devices (e.g., pacemakers) have been implanted in the body. These have typically relied for a power source on batteries implanted along with the device.

SUMMARY OF THE INVENTION

In general our invention features a new stepping motor that can be operated while totally isolated physically from any source of electrical power (i.e., without batteries and without wire connections to an external power source). The usual electromagnets used for the stator are replaced by pieces of magnetically soft and permeable material (e.g., pure iron or special alloys such as vacoperm). An externally applied magnetic field is used to magnetize the stator elements so that the localized magnetic field in the vicinity of the stator elements causes rotation of the rotor. The external magnetic field need not be applied with great precision, as the stator elements strengthen and orient the effect of the magnetic field in their vicinities.

In preferred embodiments, the stepping motor of the invention is installed in a surgically-implanted device and the magnetic field is applied from outside the body; the rotor has a plurality of permanently magnetic poles; there are a plurality of stator elements spaced around the rotor or one stator element with a plurality of lobes so spaced; the external magnetic field is applied using apparatus having a plurality of electromagnets, which are equal in number to the stator elements (or lobes of one element) and positioned similarly; and the stator elements are composed either of soft and permeable material or of such material wrapped by an electrical coil (in which is induced an electrical current, which in turn helps magnetize the soft, permeable stator material).

The invention has the advantage of allowing a mechanical movement (e.g., rotary or linear) to be induced within a device (e.g., to alter the pressure setting of a valve, to activate a switch, or to vary the parameter of an electrical circuit) without any physical connection (e.g., electrical wires) with the device.

In the medical field, it makes possible implanting a device with an internal element whose position can be accurately adjusted without the need for any wires, tubes, or other physical elements penetrating through the skin, or the use of implanted batteries. Possible applications include cerebrospinal fluid shunt valves (wherein the working pressure may be noninvasively adjusted very precisely) and implantable pumps for precise volumetric delivery of drugs.

The invention has the further advantage of being resistant to any influence from the strong magnetic fields generated by nuclear magnetic resonance (NMR) devices. Exposure to the fields of such devices will generally cause only a small incremental movement of the implanted stepping motor.

DESCRIPTION OF THE PREFERRED EMBODIMENTS

Drawings

FIG. 1 is a perspective, somewhat diagrammatic, view of a first preferred embodiment of the invention.

FIG. 2 is a cross-sectional view taken at 2—2 of FIG. 1, showing the internal construction of said first embodiment.

FIG. 3 is a cross-sectional view taken at 3—3 in FIG. 2.

FIG. 4 is an elevation view taken at 4—4 in FIG. 2.

FIG. 5 is a plan view at 5—5 in FIG. 2, showing the cam of said embodiment.

FIG. 6 is a cross-sectional view of said cam taken at 6—6 in FIG. 5.

FIG. 7 is a diagrammatic view of the steps of said cam.

FIG. 8 is a plan view of the internal support plate of said embodiment.

FIG. 8A is a cross-sectional view taken at 8A—8A in FIG. 8.

FIG. 9 is a plan view of the permanent-magnet disk of said embodiment, showing the ten pairs of poles on said disk.

FIG. 10 is a cross-sectional view of said disk taken at 10—10 in FIG. 9.

FIG. 12 is a diagrammatic view of said embodiment implanted beneath the scalp and covered by an external adjustment element.

FIG. 16 is a partial plan view, somewhat diagrammatic, of an alternative embodiment wherein the stator elements each include an electrical coil.

Structure

Figure 11:
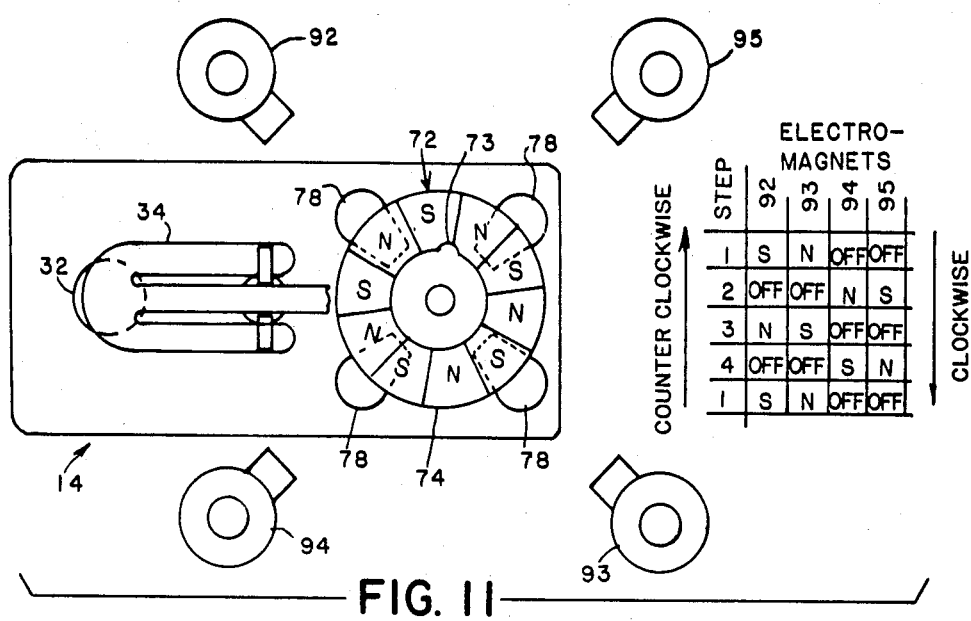
FIG. 11 is a diagrammatic view of said embodiment in which the positions of the external adjusting electromagnets are shown (much smaller than actual size).

There is shown in FIG. 1 a shunt valve assembly 10 with two shunt valves 12, 14 separated by a pumping chamber 16. Cerebroventricular catheter 18 is connected to the inlet of the valve assembly, and drainage catheter 20, to the outlet. This assembly can be surgically implanted following well-known procedures.

A cross section through the downstream shunt valve 14 is shown in FIG. 2. The upstream valve 12 is preferably the same except that the adjustment mechanism is absent. (The tubular plastic covering shown tightly fitted around the valves in FIG. 1 is not shown in the remaining figures.) Valve body 22 (injection molded from a surgically-implantable material such as polyethersulfone) has within its interior an inclined plate 24 made from a nonmagnetic material, such as titanium or stainless steel. The plate 24 has circular aperture 26 in which is press fit a sapphire ring 28, with frustoconical surface 30 forming a valve seat for spherical ball 32 (highly-polished ruby).

Biasing the ball against the valve seat is spring 34 (single piece of stainless steel or another suitable material), shown in plan view in FIG. 3. The spring provides a low K factor to produce little change in working pressure with changes in flow (i.e., a flat flow-pressure curve). The spring has base 36 overlying ball 32, central arm 38 extending from the base to an adjustment mechanism, and two flanking arms 40, 42 extending from the base to a yoke 44. The yoke is press fit into a hole in plate 24 and tabs 46 extend over the tops of the flanking arms. The yoke is relieved in the center to provide room for the central arm to pass through. Notches (not shown) cut in the ends of flanking arms 40, 42 receive portions of the yoke, and secure the spring against longitudinal movement. The spring is secured against sideward movement by contact of the flanking arms with the vertical outside surfaces of the yoke.

Plate 24 is held tightly in place within valve body 22. The tight fit is achieved by sliding the plate into the valve body (in a direction from right to left in FIG. 2). Grooves 54, 56 at the upstream end of the valve body receive portions 50, 52 (FIG. 8) of the plate, and grooves 49 at the downstream end receive tabs 48 on the plate. The grooves extend generally horizontally rather than in the inclined direction followed by the plate, and thus the tabs 48 and portions 50, 52 tend to become tightly wedged into the grooves.

Grooves 54, 56 at the ball end of the valve body also serve to press plate 24 downwardly so as to squeeze it tightly against O-ring 58 (silicone rubber), which provides an internal seal to ensure that all flow through the valve is through the orifice formed between the ball 32 and the valve seat 30. Flow through the valve is from inlet cavity 60, past ball 32, and into outlet cavity 62.

The preload of spring 34 against ball 32 is adjusted by using cam 66 (Delrin) to vary the vertical position (through a 0.75 mm range) of free end 64 of central arm 38. The spring preload establishes the pressure of the valve. The cam (best shown in FIGS. 5-7) has a circular staircase of eighteen steps, each being grooved so as to have a V-shape cross section. Free end 64 of arm 38 has a similar V-shape chosen to mate with the V-shape of steps 68. At each end of the staircase a barrier is provided by element 70. This confines rotation of the cam to slightly less than one revolution. The V-shape of steps 68 act as detents to keep the cam in precisely one of eighteen possible angular positions. That means that the vertical position of free end 64 of arm 38 is always at precisely one of eighteen different values and, in turn, that the working pressure of the valve is always at one of eighteen possible levels.

Cam 66 is press fit into the central hole in rotor 72 (4 mm diameter), with a protrusion on the cam fitting into recess 73 in the rotor to assure accurate angular positioning. The cam-rotor unit rotates loosely on shaft 76, the base of which is press fit into plate 24. The unit is retained by retaining element 77 secured to the top of the shaft. The rotor is preferably made of platinum cobalt or samarium cobalt (which may be plated with platinum to improve corrosion resistance). The rotor has ten permanently magnetic poles 74 of alternate polarity (FIGS. 9-10). At any one angular position, the pole exposed on the top surface of the disk is opposite that of the one exposed on the bottom surface.

Below rotor 72 there are fixed in place four stator elements 78 each made of a material that is magnetically soft and permeable, and that is resistant to corrosion in the presence of cerebrospinal fluid, which contains chlorides. Preferred materials include magnetic stainless steel alloys and alloys of nickel, iron, and molybdenum or cobalt. As shown in FIG. 8, the stator elements are embedded in a plastic member 80, which is fixed to plate 24 by means of shaft 76. The stator elements are shaped so that the portion of each lying beneath the rotor matches the size of permanent magnets 74. The portions of the stator elements lying radially beyond the rotor are sized to match the area beneath the rotor so that the boundary between poles, when the stator is magnetized, is at the perimeter of the rotor.

Operation

In operation the shunt valve assembly shown in FIG. 1 is surgically implanted in a patient following well-known procedures. Before implantation the pressure of adjustable valve 14 can be set to the desired level according to the circumstances of the case. For instance, it can be set approximately equal to the patient's preoperative ventricular CSF pressure so that no immediate pressure change occurs as a result of the operation. After the patient has recovered from the trauma of the operation, the pressure is adjusted downwardly to the desired level. In the case of normal-pressure hydrocephalus, the pressure is lowered to a level sufficient to initiate shrinkage of the cerebral ventricle. Further adjustments in pressure can be made at subsequent times, as necessary. In the typical treatment of normal-pressure hydrocephalus, the pressure would be adjusted upwardly after sufficient shrinkage of the ventricle has occurred in order to stabilize ventricle size.

Figure 13:
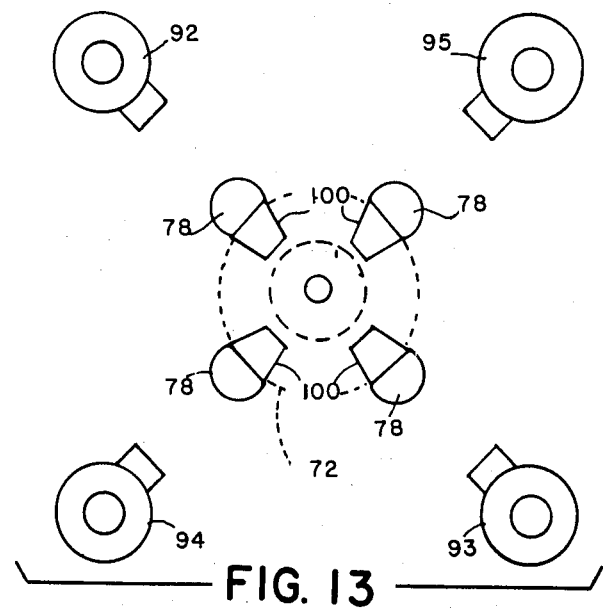
FIG. 13 is a diagrammatic view similar to FIG. 11 except that the rotor and cam have been removed to show the magnetic polarization of the four stator elements.

In children at the beginning of the treatment, the pressure should be lowered to a level inversely proportional to the ventricle size to reduce stress on the brain parenchyma (see FIG. 13 of Hakim et al., "The Physics of the Cranial Cavity", *Surg. Neurol.*, Vol. 5, March 1976), and as the ventricle decreases in size the pressure of the valve should be increased, so when the ventricle attains normal size the intraventricular pressure is again normal, thereby avoiding development in the patient of a slit-ventricle condition. Also in cases of normal-pressure hydrocephalus, sometimes in spite of a low-pressure valve the patient does not improve and the ventricle size remains unchanged, making the surgeon think he is dealing with a case of brain atrophy. But by further changing the valve pressure to a lower one, the ventricle decreases in size and the patient immediately starts to improve. In elderly persons and in long standing cases of normal-pressure hydrocephalus, it has been found that the intraventricular pressure needs to be lowered more than in young people and in hydrocephalus of short duration.

Another advantage of the invention arises in the procedure for determining when an implanted shunt valve can safely be removed from a patient, i.e., determining whether the patient is still dependent on the valve for drainage of excess cerebrospinal fluid. The conventional technique for making that determination has been to temporarily pinch closed the tube downstream of the valve and observe the patient for symptoms (e.g., slight headache) indicative of valve dependency. In the absence of symptoms the valve can be removed. With the invention it is unnecessary to stop flow entirely. A safer procedure can be followed. Valve pressure is raised, slightly at first, more so later for confirmation, using the adjustment mechanism.

Valve pressure adjustments are made by applying a pulsed magnetic field to the vicinity of the shunt valve as shown diagrammatically in FIGS. 11-13. A valve adjustment element 90 is applied over adjustable valve 14 in the orientation shown. The adjustment element contains four electromagnets 92, 93, 94, 95, which are separately controlled by an external control device, shown diagrammatically at 96. Adjustment element 90 has a marking (such as an arrow pointing in the direction of CSF flow) on its exterior to assure that it is applied to the valve in the correct orientation, and it has a groove 98 in its bottom surface sized to fit over the protrusion in the scalp, at the site of the implanted valve. The groove is narrowed at one end 99 to enable correct longitudinal alignment relative to the adjustable valve 14.

Control device 96 has input keys, which the operator uses to select one of 18 possible desired pressures (from 20 to 190 mm $H_2O$) and a pressure display.

Each of electromagnets 92, 93, 94, 95 can be energized to have either the north or south polarity facing the stator elements, or each can remain off altogether. Movement of rotor 72, in the desired direction and through the desired angle, is achieved by energizing the electromagnets in the sequence shown in the table in FIG. 11. For example, clockwise motion is achieved by first energizing electromagnets 92, 93 to south and north polarities, respectively, and leaving electromagnets 94, 95 off. In the next step electromagnets 92, 93 are left off, and electromagnets 94, 95 are energized to north and south polarities, respectively. The sequence repeats itself after the fourth step. Rotor 72 is shown in FIG. 11 in the position reached after the first step (the polarities of the rotor magnets are those on the bottom surface). If the magnetic field provided by the electromagnets is described by a vector pointing from the south to the north pole of the energized magnets, then it can be seen that the sequence prescribed for causing rotor 72 to rotate clockwise (down the table in FIG. 11) amounts to rotating the field vector in the counterclockwise direction (opposite that of the rotor), in 90° steps.

Electromagnets 92, 93, 94, 95 are positioned 90° apart and spaced equal radial distances from a central axis. When adjustment device 90 is installed properly over valve 14, the central axis of the electromagnets is coincident with the axis of rotation of rotor 72, and each electromagnet is aligned at the same angular position as one stator element 78. It is not, however, necessary that this alignment be exact. The invention is tolerant of alignment errors, which are unavoidable owing to the inability of the user to see rotor 72 or stator elements 78 and to the small size of those elements relative to the size of the external electromagnets.

The magnetic polarization induced in the stator elements 78 as the result of energizing the electromagnets is diagrammatically illustrated in FIG. 13. The two stator elements along the axis connecting the two energized electromagnets are polarized in the radial direction, so that the boundary between the poles lies roughly at the peripheral edge of disk rotor 72. The radially inner portions of these two stator elements, the portions lying beneath rotor 72, have the opposite polarity of the portions lying outside. By contrast, the stator elements along the other axis are polarized so that the boundary between poles lies along the radial direction. Both poles extend beneath the rotor 72. This pattern of polarization will result even if there is substantial error in the orientation of the electromagnets.

Movement of rotor 72 is influenced predominantly by the stator regions 100 (shown in dashed lines in FIG. 13) lying beneath the rotor, as it is those portions that are closest to the permanent magnets 74 of the rotor. Accordingly, the part of the stator elements with uniform polarity dominate over those with split polarity. This phenomenon could be emphasized by making the stator elements of a magnetically anisotropic material so that the magnetization induced by the external electromagnets is strongest along the radial axis of the corresponding stator elements.

The number of magnetic poles 74 is selected so that when one pair of radially opposite stator elements 78 is aligned with one pair of magnetic poles 74 (as are the upper left and lower right stator elements in FIG. 11) the other two stator elements (the upper right and lower left in FIG. 11) are each staggered halfway between two of the poles 74. In operation, control device 96 energizes the electromagnets closest to the pair of stators staggered between two magnets, thereby causing the rotor to move through an angle corresponding to one half the width of a magnetic pole 74.

In the preferred embodiment there are ten magnetic poles on each side of the disk, and thus twenty angular increments in one full revolution (i.e., each step is one twentieth of 360°, or 18°). Only eighteen of these increments are used, corresponding to the eighteen detented steps along the staircase surface of cam 68 (the other two increments are occupied by the detent wall 70 of the cam).

After a pressure is prescribed on control device 96, an enter key is pressed. That initiates a sequence of eighteen steps in the direction of lower pressure settings, counterclockwise rotation of rotor 72. This assures that the cam is returned to a position wherein spring arm 64 is at the lowest step on the cam staircase. If fewer than eighteen steps are actually needed to bring the cam to this position (as will most often be the case), the detent wall provided by element 70 of the cam prevents further rotation. After the eighteen-step resetting sequence is complete, the rotor is moved clockwise by the number of steps corresponding to the prescribed pressure.

Other Embodiments

Other embodiments are within the scope of the following claims, for example:

The invention could be used in nonmedical applications.

A magnetically anisotropic material could be used for the stator elements, with the strongest axis of magnetization oriented along the radial direction. Such anisotropy could also be achieved mechanically by splitting each stator element along the radial direction into two or more segments.

A variable reluctance or hybrid rotor could replace permanent-magnet rotor 72.

Linear movements within an implanted device could be achieved following the invention by providing a linearly-moving element as the rotor and by placing stator elements along the path of the linearly-moving rotor.

A rotor with fewer poles could replace the ten-pole rotor of the preferred embodiment, particularly where fine angular precision is not required (e.g., in a pump a simple two-pole rotor might suffice). Strong permanent magnets could be used to apply the external field (e.g., in the two-pole rotor of the pump application just described).

Electrical wire could be wrapped around the implanted stator elements forming a coil so that an electrical current is induced therein by the externally-pulsed magnetic field; the electrical current would in turn magnetize the stator elements if the coil circuit is closed by a resistor or a capacitor.

Figure 14:
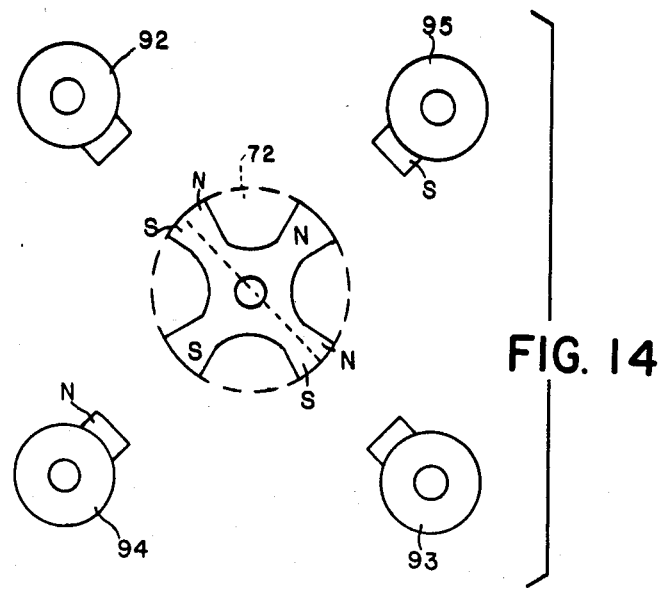
FIGS. 14 and 15 show the magnetic polarization of an alternative embodiment, where a one-piece stator element is used.
Figure 15:
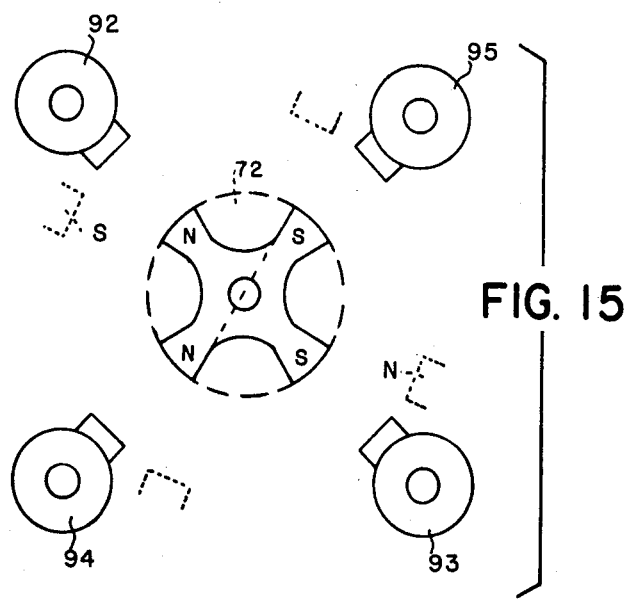

A single-piece stator element, e.g., with four lobes as shown in FIG. 14, could replace the stator elements of the preferred embodiment. An advantage of using a single-piece stator element is that the stator can lie entirely inside of the outer perimeter of the rotor, and thus provide for a more compact implanted unit. This is because, when magnetized, as shown in FIG. 14, the dominating lobes are all of one polarity, rather than split radially into two polarity regions as in the preferred embodiment. Thus the entire lobe, not just the inner half, can be influential in moving the rotor. The disadvantages of the single-piece stator is its lower tolerance to errors in alignment of the external magnetic field. The reduced tolerance for misalignment can be understood by reference to FIG. 15, in which the external field has been rotated sufficiently to cause the lobes that were split into two poles to now be entirely within the region of one pole. As a result all four lobes have nearly equal influence on the rotor, and it is not possible to move the rotor.

A presently even more preferred embodiment is one having a rotor 72 with six poles rather than ten (as shown in the figures). Such a rotor provides twelve steps of 30° for one full revolution. Eleven of these can be used to provide eleven different pressure settings (each differing by 15 mm $H_2O$) from 30 to 180 mm $H_2O$. An advantage of six poles is that with the four-stator-element configuration (FIG. 11) greater torque is available using six rather than ten poles. This results because all four stator elements, when magnetized by the external field, generate a torque in the same direction. In the ten-pole embodiment (FIG. 11), this is not the case. The torque generated by the stator elements with split polarity (upper right and lower left in FIG. 11) is opposite, though weaker, that generated by the stator elements with uniform polarity. It is instructive to note, however, that this difference between the six and ten-pole embodiments is just the opposite if a one-piece, four-lobed stator is used. In that case, the split polarity stator elements generate opposing torque with the six-pole rotor and not with the ten-pole one. Also, if a ten-pole rotor is used with separate stator elements, torque can be increased by using anisotropic material for the stator elements, as that will increase the dominance of the uniform polarity stator elements over the split polarity ones.

We claim:

1. Surgically-implantable apparatus such as a valve, pump, or pacemaker, said apparatus including a stepping motor for adjusting said apparatus, said stepping motor being isolated physically from electrical power sources and powered by the influence of an external magnetic field applied from outside the apparatus, said stepping motor comprising a rotor,
   one or more stator elements,
   means for mounting said rotor so that it is capable of movement relative to said stator elements,
   said stator elements being composed of magnetically soft and permeable material shaped and positioned with respect to said rotor so that when magnetized under the influence of said external field the said stator elements strengthen and orient the magnetic field in their vicinities so as to cause incremental movement of said rotor,
   means for positioning said rotor with respect to said stator elements so that when said stator elements are magnetized under the influence of said external field incremental movement of said rotor occurs,
   wherein said apparatus is adapted to be surgically-implanted and said magnetic field is applied from outside the body.

2. The apparatus of claim 1 wherein said rotor has pemanently magnetic regions.

3. The apparatus of claim 1 or 2 wherein there are a plurality of said stator elements spaced angularly around the perimeter of said rotor.

4. The apparatus of claim 1 or 3 wherein there is one stator element having a plurality of lobes extending from a central region, said lobes being spaced angularly around the perimeter of said rotor.

5. The apparatus of claim 1 combined with external apparatus for generating said externally applied magnetic filed, said external apparatus comprising a plurality of electromagnets and control means for selectively energizing said electromagnets in a sequence that causes said stator elements to be magnetized in successive angular steps causing the rotor to move.

6. The apparatus of claim 5 wherein said electromagnets have the same angular spacing around a central axis as said stator elements have around the rotor axis so that said external apparatus can be positioned with said axes coincident and with said electromagnets at the same angular orientations as said stator elements.

7. The apparatus of claim 1 wherein said stator elements include electrical coils, said coils being positioned with respect to said stator elements so that an electrical current induced in said coils by said magnetic field magnetizes said stator elements.

8. The apparatus of claim 1 or 7 wherein there are either a plurality of said stator elements or one stator element with separated lobes and wherein said stator elements or lobes are positioned so that particular regions thereof have greatest effect on movement of said rotor, and wherein said stator elements are positioned so that by variation in orientation in said externally applied magnetic field selected ones of said regions can be made either all one polarity or all the other polarity or split between both polarities, whereby the regions of one polarity can dominate over the regions of split polarity in controlling movements of said rotor.

9. The apparatus of claim 8 wherein there are a plurality of said stator elements and each is positioned so that the radially inner half thereof is closest to the magnetically active regions of said rotor and thereby forms said region of greatest influence.

10. The apparatus of claim 9 wherein there are at least four said stator elements equally spaced around the perimeter of said rotor so that under the influence of an external magnetic field two radially opposing elements have said regions of all one polarity and the other two elements have said regions of split polarity.

11. The apparatus of claim 1 wherein said apparatus is an implanted cerebrospinal fluid shunt valve and comprises a mechanism for adjusting the pressure of said valve and means for connecting said rotor to said mechanism so that movement of said rotor in response to said applied external magnetic field causes adjustment of the pressure of said valve.

12. The apparatus of claim 11 wherein said valve includes a valve element and said adjustment mechanism comprises a cam adapted to rotate with said rotor and a spring with two portions, one portion engaging said valve element to provide a preload thereon and another portion engaging said cam, and means for mounting said spring so that said preload varies in response to rotation of said cam.

13. The apparatus of claim 1 wherein said stator elements are magnetically anisotropic so that they are more strongly magnetized along the radial direction with respect to said rotor.

14. The method of surgically implanting a device and later adjusting its operation from outside the body, comprising surgically implanting a device having a stepping motor, said stepping motor being physically isolated from electrical power sources and comprising a rotor and one or more stator elements, said stator elements being composed of magnetically soft and permeable material shaped and positioned with respect to said rotor so that when magnetized the local magnetic fields in their vicinities cause rotation of said rotor, applying from outside the body a magnetic field so as to magnetize said stator elements to cause movement of said rotor.

15. A stepping motor for producing incremental movement within a structure, said motor comprising an external unit for placement outside said structure, said external unit comprising one or more members for generating a time-varying external magnetic field, an internal unit for placement inside said structure, said internal unit comprising a rotor, one or more stator elements each composed of a magnetically soft and permeable material, said stator elements being spaced from said rotor by a gap, means for mounting said rotor so that it is capable of movement relative to said stator elements, said stoator elements being shaped and positioned with respect to said rotor so that when magnetized under the influence of said external magnetic field said stator elements strengthen and orient the magnetic field in their vicinities so as to cause incremental rotation of said rotor, means for positioning said rotor with respect to said stator elements so that when said stator elements are magnetized under the influence of said external field incremental movement of said rotor occurs, said external and internal units being so constructed that said external unit may be positioned remotely from said internal unit during use, and said external and internal units being so constructed that in use the spacing of said field-generating members in said external unit from said stator elements is greater than said gap between said stator elements and said rotor.

16. The stepping motor of claim 15 wherein said internal unit is adapted to be surgically-implanted and said external unit is adapted to be used from outside the body.

17. The stepping motor of claim 15 wherein said members are electromagnetic that remain fixed in place and means are provided for selectively energizing different ones of said electromagnets to generate said time-varying magnetic field.

18. The apparatus of claim 2 or 15 wherein means are provided for mounting said rotor for rotation.

* * * * *